United States Patent
Bai et al.

(10) Patent No.: US 9,092,811 B2
(45) Date of Patent: Jul. 28, 2015

(54) GUIDELINE-BASED FOOD PURCHASE MANAGEMENT

(75) Inventors: Kun Bai, Elmsford, NY (US); Ming Li, Elmsford, NY (US); Leslie S. Liu, White Plains, NY (US); Fan Ye, Ossining, NY (US); Liangzhao Zeng, Mohegan Lake, NY (US); Xinxin Zhu, Croton on Hudson, NY (US)

(73) Assignee: International Business Machines Corporation, Armonk, NY (US)

( * ) Notice: Subject to any disclaimer, the term of this patent is extended or adjusted under 35 U.S.C. 154(b) by 172 days.

(21) Appl. No.: 13/150,350

(22) Filed: Jun. 1, 2011

(65) Prior Publication Data

US 2012/0310758 A1    Dec. 6, 2012

(51) Int. Cl.
G06Q 30/00 (2012.01)
G06Q 30/06 (2012.01)
G06F 19/00 (2011.01)
G06Q 30/02 (2012.01)

(52) U.S. Cl.
CPC ........ G06Q 30/0601 (2013.01); G06F 19/3475 (2013.01); G06Q 30/0205 (2013.01); G06Q 30/0633 (2013.01); G06Q 30/0643 (2013.01)

(58) Field of Classification Search
CPC ................ G06Q 30/0633; G06Q 30/0643
USPC ........ 705/10, 14, 15, 23, 26.1, 2, 26.8, 26.81, 705/26.9, 27.1, 27.2
See application file for complete search history.

(56) References Cited

U.S. PATENT DOCUMENTS

| | | | |
|---|---|---|---|
| 5,454,721 A | 10/1995 | Kuch | |
| 5,937,387 A | 8/1999 | Summerell et al. | |
| 6,304,855 B1 * | 10/2001 | Burke | 705/26.9 |
| 6,620,078 B2 | 9/2003 | Pfeffer | |
| 7,231,357 B1 * | 6/2007 | Shanman et al. | 705/14.23 |
| 7,809,153 B2 | 10/2010 | Bravomalo et al. | |
| 2002/0027164 A1 * | 3/2002 | Mault et al. | 235/462.46 |
| 2003/0120515 A1 | 6/2003 | Geller | |
| 2003/0171944 A1 * | 9/2003 | Fine et al. | 705/1 |
| 2006/0064447 A1 | 3/2006 | Malkov | |
| 2006/0187025 A1 | 8/2006 | Engstrom et al. | |
| 2006/0199155 A1 * | 9/2006 | Mosher | 434/127 |
| 2006/0205564 A1 | 9/2006 | Peterson | |
| 2008/0086374 A1 * | 4/2008 | Aitken et al. | 705/14 |
| 2008/0161733 A1 | 7/2008 | Einav et al. | |
| 2010/0070338 A1 * | 3/2010 | Siotia et al. | 705/10 |
| 2010/0070888 A1 | 3/2010 | Watabe et al. | |
| 2010/0131377 A1 * | 5/2010 | Karnalkar et al. | 705/26 |
| 2010/0198626 A1 * | 8/2010 | Cho et al. | 705/10 |
| 2012/0136731 A1 * | 5/2012 | Kidron et al. | 705/15 |

* cited by examiner

Primary Examiner — Hunter Wilder
(74) Attorney, Agent, or Firm — Ryan, Mason & Lewis, LLP

(57) ABSTRACT

A system and computer program product for guideline-based food purchase management include generating a personalized set of nutrition guidelines for a user, generating a user profile for the user, wherein the user profile comprises health information and nutrition preferences, and using the personalized set of nutrition guidelines and the user profile to generate a guideline-based shopping list for the user.

8 Claims, 7 Drawing Sheets

GUIDELINE-BASED FOOD PURCHASE MANAGEMENT

FIELD OF THE INVENTION

Embodiments of the invention generally relate to information technology, and, more particularly, to health management.

BACKGROUND OF THE INVENTION

Existing nutrition control guidelines and management approaches include challenges in being difficult to follow for individuals. For example, many approaches are not personalized, and can have difficulties in linking nutrition guidelines with a list of food to purchase. Additionally, many existing approaches lack dynamic re-planning of food list according to users' preference (making it difficult, for example, to satisfy all members in a family), and lack real-time guidance during shopping.

SUMMARY OF THE INVENTION

Principles and embodiments of the invention provide techniques for guideline-based food purchase management. An exemplary method (which may be computer-implemented) for guideline-based food purchase management, according to one aspect of the invention, can include steps of generating a personalized set of one or more nutrition guidelines for a user, generating a user profile for the user, wherein the user profile comprises health information and one or more nutrition preferences, and using the personalized set of one or more nutrition guidelines and the user profile to generate a guideline-based shopping list for the user.

Also, an exemplary method (which may be computer-implemented) for generating location-based food purchase guidance, according to one aspect of the invention, can include steps of obtaining a shopping list of one or more food items and a list of one or more stores to be considered in connection with the one or more food items on the shopping list, using the shopping list, list of one or more stores, a store location map and inter-store routing guidance to generate an inter-store shopping route, and generating an in-store shopping route, for each of the one or more stores in the inter-store shopping route, based on the shopping list of one or more food items, intra-store routing guidance and a floor plan for the store.

One or more embodiments of the invention or elements thereof can be implemented in the form of a computer product including a tangible computer readable storage medium with computer useable program code for performing the method steps indicated. Furthermore, one or more embodiments of the invention or elements thereof can be implemented in the form of an apparatus including a memory and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s), or (iii) a combination of hardware and software modules; any of (i)-(iii) implement the specific techniques set forth herein, and the software modules are stored in a tangible computer-readable storage medium (or multiple such media).

These and other objects, features and advantages of the present invention will become apparent from the following detailed description of illustrative embodiments thereof, which is to be read in connection with the accompanying drawings.

DETAILED DESCRIPTION OF EMBODIMENTS

Principles of the invention include a system and techniques for an evidence-based food purchase management mobile application. As detailed herein, in one or more embodiments of the invention, a guideline-based food purchase management mobile application can include a personalized nutrition guideline, an evidence-based shopping list creation, a location-based food purchase guidance, as well as real-time nutrition compliance tracking.

Nutrition control can often start from food purchase. In current nutrition control practice, users can be educated and guided with healthy recipes. For example, users may receive nutrition guidelines such as a suggested number of servings of carbohydrates, vegetables, and fruit, as well suggested foods. However, such guidelines are often not practicable, as difficulties may arise, for example, when buying foods according to the nutrition guideline, especially when food purchasing is occurring for multiple people and/or members of a family.

One or more embodiments of the invention include a mobile solution that can provide food purchase management on a handhold device. With a mobile application such as detailed herein, users can create a food shopping list according to the availability of selected food markets based on personalized nutrition guidelines. Further, during the shopping, one or more embodiments of the invention include a graphic dashboard that indicates the progress of confirmation on nutrition guidelines. Further yet, users can dynamically adjust the shopping list while still conforming to nutrition guidelines.

Figure 1:
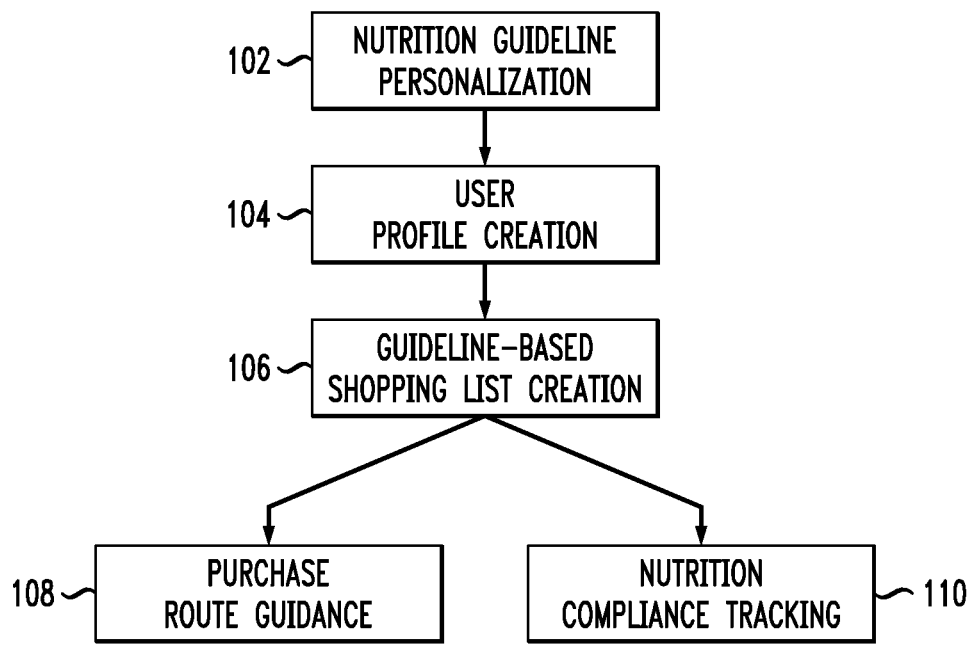
FIG. 1 is a flow diagram illustrating techniques for guideline-based food purchase management, according to an embodiment of the present invention.

FIG. 1 is a flow diagram illustrating techniques for guideline-based food purchase management, according to an embodiment of the present invention. Step 102 includes nutrition guideline personalization. Step 104 includes user profile creation. Step 106 includes guideline-based shopping list creation. Step 108 includes location-based food purchase guidance. Further, step 110 includes real-time nutrition compliance tracking.

Figure 2:
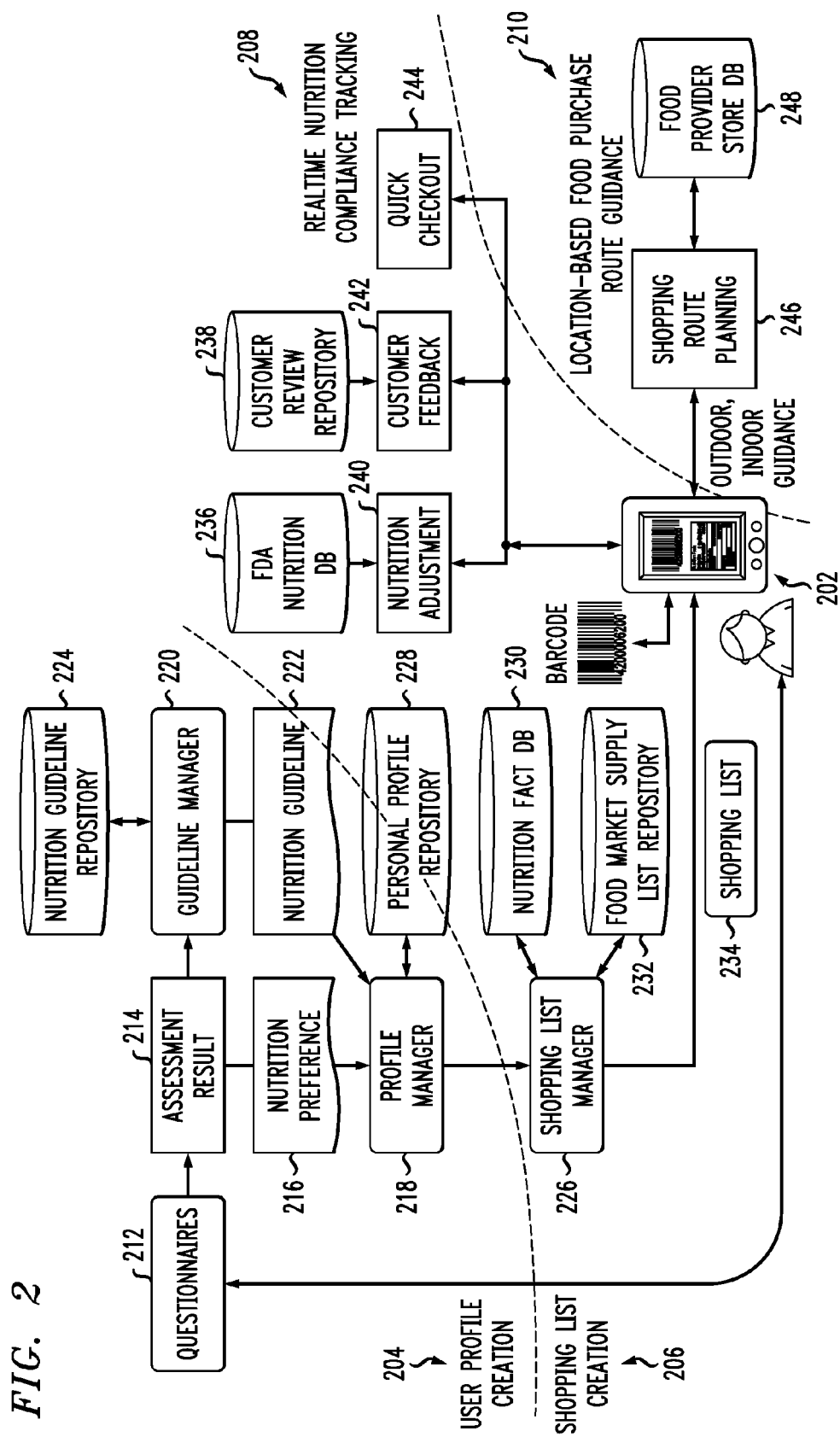
FIG. 2 is a diagram illustrating system architecture for guideline-based food purchase management, according to an embodiment of the present invention.

FIG. 2 is a diagram illustrating system architecture for guideline-based food purchase management, according to an embodiment of the present invention. By way of illustration, FIG. 2 depicts nutrition guideline personalization and user profile creation. Specifically, FIG. 2 depicts a user (and/or a user's mobile device) 202, a user profile creation phase 204, a shopping list creation phase 206, a real-time nutrition compliance tracking phase 208 and a location-based food purchase route guidance phase 210.

In the user profile creation phase 204, through Web-enabled questionnaires 212, the system will collect and assess the information such as the following (for example) from users: demographics, personal health status, family medical history, and shopping preferences. In one or more embodiments of the invention, the questionnaires can be conducted, for example, for first-time users on a per family basis. Each family member can also give a personal preference list about what food/drink/fruit/etc. he or she likes/dislikes, regardless of nutrition constraints. The assessment result 214 is used in two aspects. First, the assessment result 214 is used by guideline manager 220 to select an appropriate nutrition guideline 222 from the repository 224. It should be noted that nutrition selection can be evolved according to changes of person's wellness condition. For example, based on progression of a person's chronic disease, the nutrition guideline may need to be adjusted.

Second, the assessment result 214 also provides a user's personal preference 216 on her/his food intake.

The user profile is created based on selected nutrition guideline 222 and preference 216. A user (for example, a family member) can change original answers anytime in order to modify his or her profile. Once the profiles are set up, their data will be analyzed by a profile manager 218, an evidence-based decision support system, to generate appropriate food recommendations for each user (for example, family member) and to compile a shopping list 234 for the users (for example, for an entire family) via a shopping list manager 226. Also, profiles can be stored in a personal profile repository 228.

With respect to the guideline-based shopping list generation, one or more embodiments of the invention include using a food list filter and categorization mechanism. This includes accessing food market supply list repository 232 and personalized guidelines, and divides candidate food into categories such that food in the same category is interchangeable. Additionally, with user input such as budget, driving distances, preferred stores, available coupons from each store, etc., the shopping list manager 226 uses information in a personal profile (provided by profile manager 218), and accesses a nutrition fact database 230 and a food market supply list repository 232 to generate optimized shopping list 234.

Additionally, as detailed herein, FIG. 2 depicts a real-time nutrition compliance tracking phase 208, which includes the use of a Food and Drug Administration (FDA) nutrition database 236 to make any desired nutrition adjustments 240, a customer review repository 238 used in conjunction with customer feedback 242 and a quick checkout component 244. Also, as noted, FIG. 2 depicts a location-based food purchase route guidance phase 210 which includes a shopping route planning component 246 and a food provider and store database 248.

Figure 3:
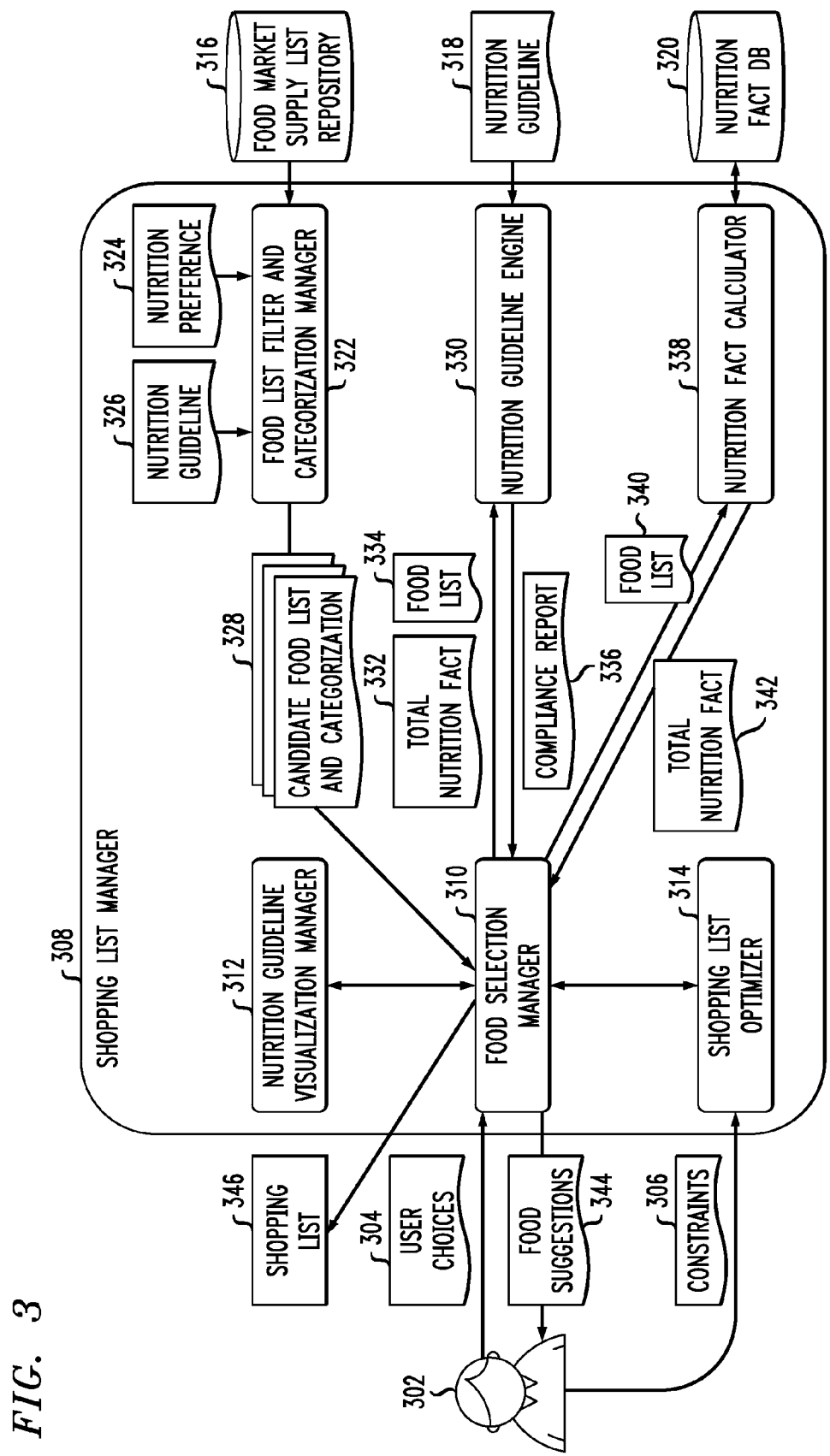
FIG. 3 is a diagram illustrating a shopping list manager, according to an embodiment of the present invention.

FIG. 3 is a diagram illustrating a shopping list manager, according to an embodiment of the present invention. By way of illustration in FIG. 3, guideline-based shopping list generation includes a user 302 interactively selecting items 304 to purchase, with a food compliance report 336 updated in real time while the shopping list manager 308 provides food suggestions 344 to the user.

As depicted in FIG. 3, a food list filter and categorization manager 322 accesses a food market supply list repository 316 and uses personalized nutrition guidelines 326 and preference 324 specified in a user profile to filter out foods that are not suitable for the user(s). For these good candidate items, the system divides items into categories such that items within the same category are replaceable (for example, the foods have similar combination of nutrients but with different flavors/price). By way of example, both milk and cheese are high in calcium, but their fat/salt content might be different.

Based on candidate items and categorization 328, the users can interactively select items. A user interface (UI) can show multiple bars of multiple types, such as one for the minimum amount of necessities (for example, folic acid for pregnant women) and one for the maximum amount of avoidances (for example, sugar for diabetes patients). Based on the constraints 306 on nutrition and/or budget provided to the shopping list optimizer component 314, the user is asked to make selections 304 in each category from a list of available items (for example, to select fruits from apples, oranges, bananas, avocados, etc.). These items can be shown partly based the preference list. Preferred items can be shown, for example, with a highlighted color or ordered earlier so it is easier for users to select them. Here, the system relies on a nutrition fact calculator 338 (which receives input from a nutrition fact database 320) that computes total nutrition fact 342 based on the provided food list 340. The total nutrition fact 342 is provided to the food selection manager 310, which interacts with the nutrition guideline visualization manager 312 to create a visualized report to indicate a healthy choice of food. The food selection manager 310 also ultimately outputs the shopping list 346.

During the food list creation, the food selection manager 310 also sends total nutritional fact 332 and food list 334 to a nutrition guideline engine 330 (which receives nutrition guidelines 318) to generate a compliance report 336, in order to give awareness of compliance.

Each time a user makes a selection, measurements are updated based on the nutrition in the chosen item. The changes in current necessities and avoidances can help the user make further selections, indicating how much necessities he or she still needs, or if he or she has gone beyond the limit of avoidances. In such cases, the UI can give suggestions about which items to choose/remove.

Figure 4:
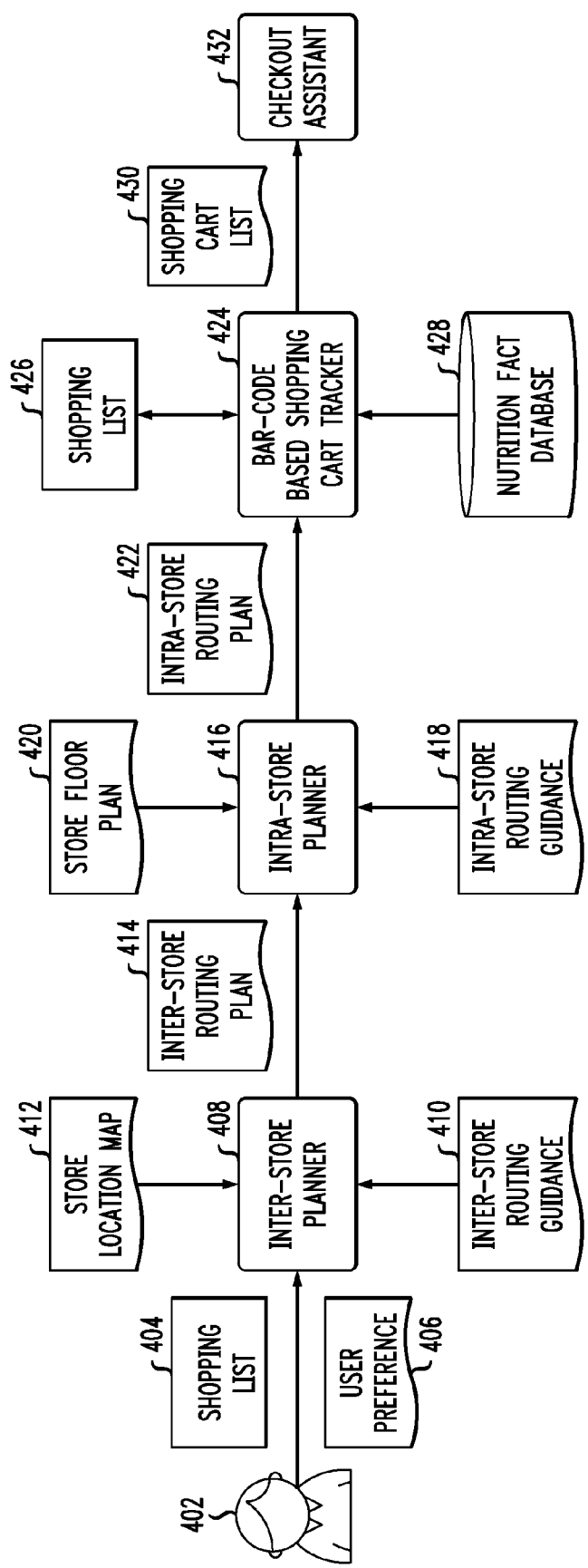
FIG. 4 is a diagram illustrating location-based food purchase route guidance, according to an embodiment of the present invention.

FIG. 4 is a diagram illustrating location-based food purchase route guidance, according to an embodiment of the present invention. Given a shopping list 404 and a list of stores in the shopping list (as well as, in one or more embodiments of the invention user preference 406), an inter-store planner 408 plans the optimum shopping route based on additional input such as a store location map 412 and other inter-store routing guidance 410. Users 402 have multiple options in route planning, such as, for example, the shortest path passing all stores, visiting favorite stores first, and visiting stores with lower price first. Some general guidelines (such as depicted via component 410) are applied to all options (for example, always buy frozen/hot food at the end of a shopping trip). Accordingly, the inter-store planner 408 outputs an inter-store routing plan 414.

The system can also alert users based on their locations. For instance, when a user is passing by a store on the list, his/her phone will remind him/her by audio/visual message.

Additionally, when a user enters a store, the intra-store planner 416 plans his/her in-store route 422 based on the shopping list 404 and the store's floor plan 420. There are also multiple guidelines 418 for this route planning, such as, for example, the shortest path passing all items on the shopping list, picking-up frozen/hot food last, picking-up heavy items last, picking-up bulky items first, exiting through the shortest checkout queue if the store provides real-time information on the queue length, etc. Users can give different preferences 406 to different guidelines.

During the shopping process, users can scan barcodes of items (for example, items from the shopping list 426) via a barcode-based shopping cart tracker 424 (using, for example, a mobile phone application) and check price and nutrition facts (using information provided by a nutrition fact database 428). Such a mobile phone application can also track the total cost, etc. During checkout, the barcode-based shopping cart tracker 424 can provide the shopping cart list 430 to a checkout assistant component 432. Further, users can show coupons on smart phones to cashiers, and the checkout assistant can help users to verify if the checkout process is correct.

Figure 5:
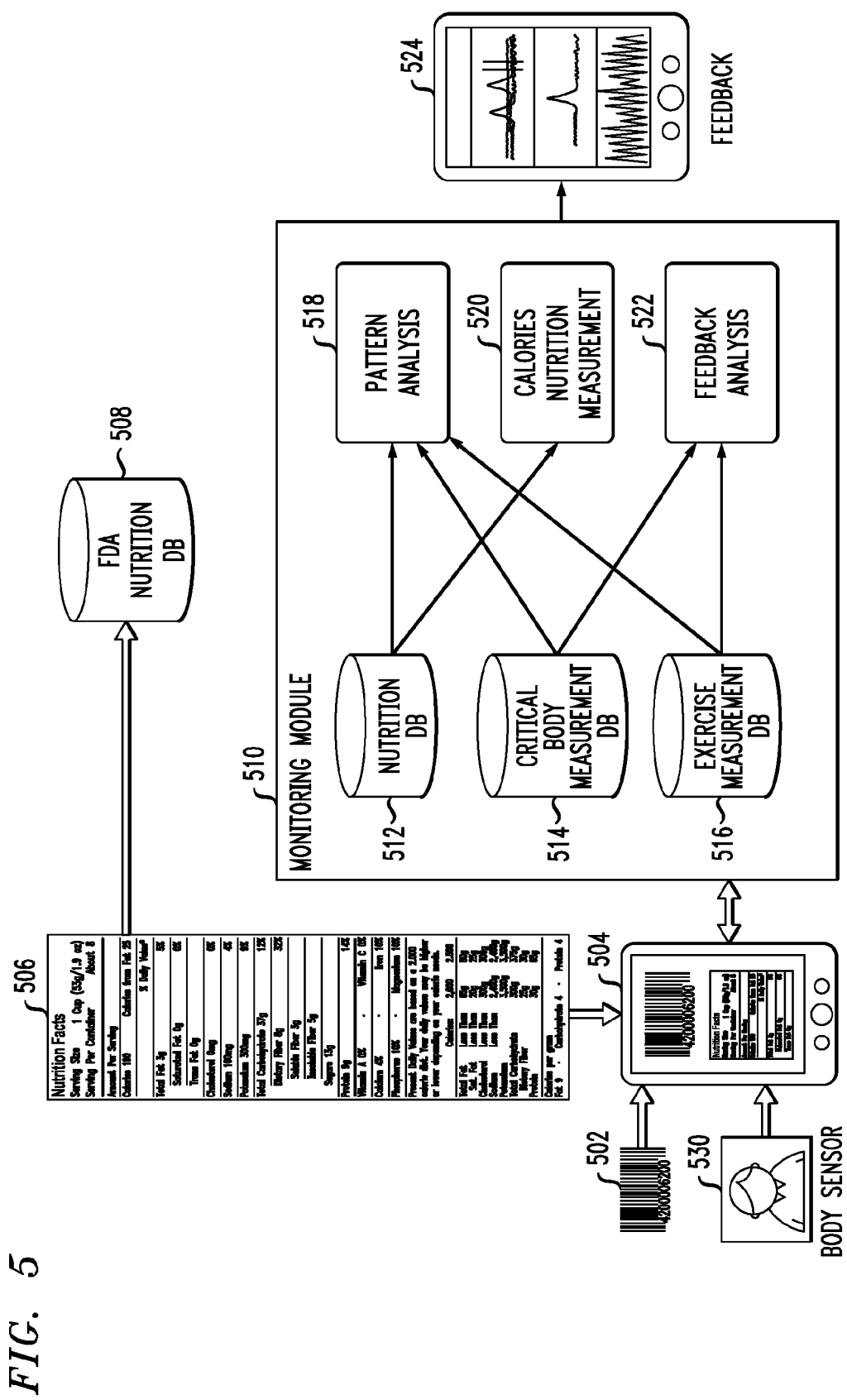
FIG. 5 is a diagram illustrating real-time nutrition compliance tracking, according to an embodiment of the present invention.

FIG. 5 is a diagram illustrating real-time nutrition compliance tracking, according to an embodiment of the present invention. During a food purchase, one or more embodiments of the invention can also help end-users to make ad-hoc decisions based on nutrition compliance status. For example, a user may pickup an item which is not in the generated shopping list. In such a case, the system will generate new visualized compliance report and may automatically adjust the item list with the item that is yet to be picked-up.

Accordingly, as depicted in FIG. 5, one or more embodiments of the invention include run-time nutrition adjustment by barcode reading using a mobile device 504. When a user (family member) goes shopping with a generated shopping list as detailed herein, he/she might find some new products that are not on the shopping list, but he/she would like to know if such a product could be a proper substitution to one existing on the list. The barcode reader component in the system can quickly scan the desired product, obtain the barcode 502, and then query locally or remotely the nutrition facts 506 about this product from a nutrition database 508. Based on the queried nutrition facts 506, a nutrition analysis can be conducted and conclude if the new product is a proper substitution. If not, a suggestion/recommendation can be made if other items combined with this new product might be a good combined nutrition solution.

Also, under some circumstances, a new (or a proper substitution) product can match up to the nutrition requirements calculated by the system, even though its custom review/feedback may not as positive as expected. This information might be very useful, but not always be available to the shopper when he/she is shopping inside a store. As such, by reading the barcode 502, such information can be queried locally or remotely by one or more embodiments of the invention and be prompted to the shopper as decision assistance.

Additionally, a barcode reader component can also help the shopper to check-out. For example, as the shopper goes into a store, the store's price database (DB) can be synced-up with the shopper's local DB on his or her mobile device 504. Every time the shopper scans a product (item) on the shopping list, the item will be moved to a shopping-cart (on the mobile device), and the price of the item will be queried locally and added to a total amount. When the shopper finishes his/her task, he/she could self-check-out and pay the amount via modern mobile payment system, such as near field communication (NFC), etc.

Further, one or more embodiments of the invention includes tracking users' running/walking distance based on global positioning system (GPS) and accelerometer readings. Based on GPS, a mobile phone application can detect if a user is moving or stationary, how fast he/she is moving, and for how far a distance. Based on accelerometer, the mobile phone application can detect if the user is driving, walking, climbing stairs, or running. Then the mobile phone application can calculate how much calories the user consumes during these activities.

One or more embodiments of the invention (via a mobile phone application, as detailed herein) can also track users' activities in gyms or other exercise venues. For example, running/walking on treadmills or eclipse machines, and climbing on stair machines can be tracked by accelerometer via a body sensor 530 (as described above). When users use weight machines, they can take pictures of the machines' barcodes, labels, or just the machines. The mobile phone application searches for the machines' profiles based on the pictures. Also, users can easily enter the amount of exercise they do on these machines, for instance, how many lifts or push-ups on the machines. The mobile phone application can calculate users' calorie consumption during these activities based on the collected information.

Users can also use the mobile phone application to track daily nutrition intake. Before each meal, the user can take pictures of the food he or she will eat using a smart phone 504. The mobile phone application then sends the pictures to back-end servers and gets back nutrition facts of the meals. Users can also input this information manually any time on the mobile phone application or to a web-based interface on computers. For example, the mobile phone application can provide relevant input to a monitoring module 510, which will utilize a nutrition database 512, a critical body measurement database 514 and an exercise measurement database 516 to provide pattern analysis 518, calories nutrition measurement 520 and feedback analysis 522, as well as ultimately provide feedback 524 to the mobile device.

Further, based on users' wellness status and nutrition intake, one or more embodiments of the invention can also generate and update systematic exercise plans for users. The mobile phone application will remind users to do exercises based on the plans.

Figure 6:
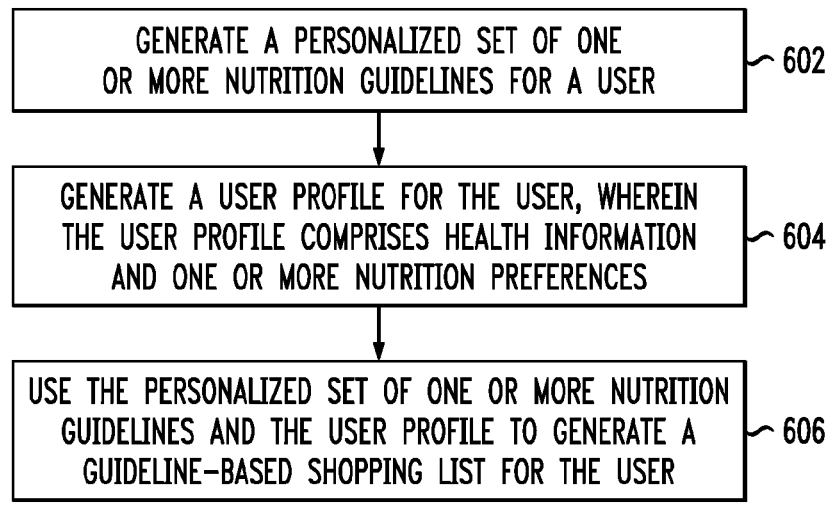
FIG. 6 is a flow diagram illustrating techniques for guideline-based food purchase management, according to an embodiment of the invention.

FIG. 6 is a flow diagram illustrating techniques for guideline-based food purchase management (for example, implemented on a handheld mobile device), according to an embodiment of the present invention. Step 602 includes generating a personalized set of one or more nutrition guidelines for a user. This step can be carried out, for example, using a guideline manager module. Step 604 includes generating a user profile for the user, wherein the user profile comprises health information and one or more nutrition preferences. This step can be carried out, for example, using a profile manager module.

Generating a personalized set of nutrition guidelines and generating a user profile include using Web-enabled questionnaires to collect and assess information pertaining to the user (such as, for example, demographics, personal health status, family medical history, shopping preferences, etc.). Generating a personalized set of nutrition guidelines further includes using an assessment of the information to select an appropriate set of one or more nutrition guidelines from a nutrition guideline repository. Additionally, generating a user profile further includes using an assessment of the information and the appropriate set of nutrition guidelines to generate the user profile.

Step 606 includes using the personalized set of one or more nutrition guidelines and the user profile to generate a guideline-based shopping list for the user. This step can be carried out, for example, using a shopping list manager module. Using the personalized set of nutrition guidelines and the user profile to generate a guideline-based shopping list includes using information pertaining to availability of one or more selected food markets based on the personalized set of nutrition guidelines. Also, using the personalized set of nutrition guidelines and the user profile to generate a guideline-based shopping list includes accessing a food market supply list repository and dividing candidate food into one or more categories such that food in a same category is interchangeable.

Additionally generating the guideline-based shopping list further includes using additional user input pertaining to user budget, travel distance of one or more stores, user preference of one or more stores, and available coupons from one or more stores, etc. Generating the guideline-based shopping list further includes facilitating a user to interactively select one or more items to purchase, and updating a food compliance report in real-time and providing one or more food suggestions to the user based on the selected items. Updating a food compliance report in real-time can include using a nutrition fact calculator to compute a total nutrition fact based on the selected items and input from a nutrition fact database.

Further, using the personalized set of nutrition guidelines and the user profile to generate a guideline-based shopping list can include accessing a food market supply list repository and filtering out one or more foods that are not suitable for the user.

Figure 7:
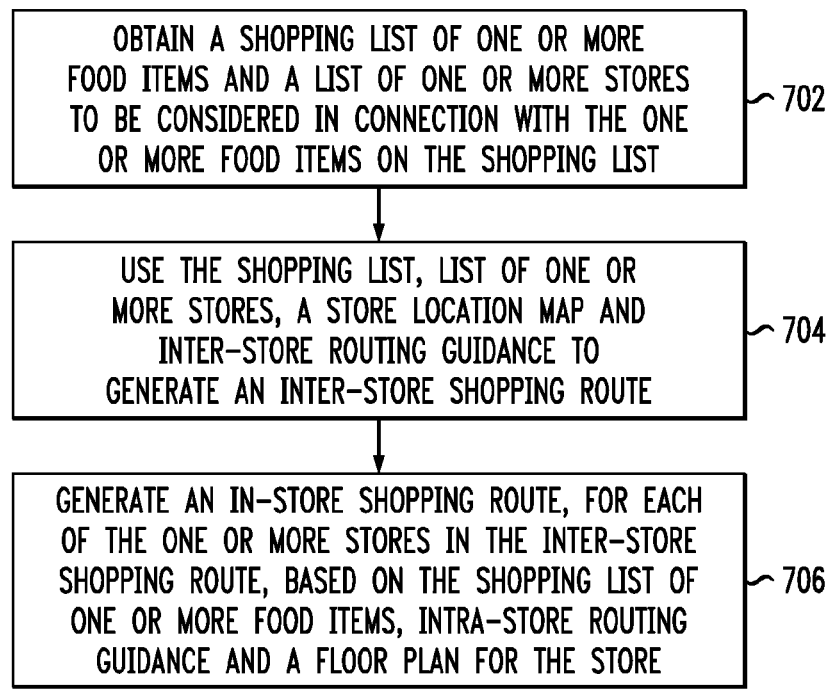
FIG. 7 is a flow diagram illustrating techniques for generating location-based food purchase guidance, according to an embodiment of the invention.

FIG. 7 is a flow diagram illustrating techniques for generating location-based food purchase guidance, according to an embodiment of the present invention. Step 702 includes obtaining a shopping list of one or more food items and a list of one or more stores to be considered in connection with the one or more food items on the shopping list. Step 704 includes using the shopping list, list of one or more stores, a store location map and inter-store routing guidance to generate an inter-store shopping route. This step can be carried out, for example, using an inter-store planner module.

Step 706 includes generating an in-store shopping route, for each of the one or more stores in the inter-store shopping route, based on the shopping list of one or more food items, intra-store routing guidance and a floor plan for the store. This step can be carried out, for example, using an intra-store planner module. Guidelines for intra-store route planning can include, for example, the shortest path passing all items on the shopping list, picking-up frozen/hot food last, picking-up heavy items last, picking-up bulky items first, exiting through the shortest checkout queue if the store provides real-time information on the queue length, etc.

Generating an in-store shopping route further includes using one or more user preferences in connection with the intra-store guidance.

The techniques depicted in FIG. 7 can additionally include obtaining one or more user preferences in connection with the one or more stores. Additionally, one or more embodiments of the invention can include alerting a user of shopping information based on locations of the user.

Also, the techniques depicted in FIG. 7 can include using a user-scanned barcode of an item during shopping, via a barcode-based shopping cart tracker module, to check price and one or more nutrition facts of the item. Using a user-scanned barcode of an item during shopping to check one or more nutrition facts of the item includes tracking real-time nutrition compliance for a user, as well as using the nutrition facts of the item to suggest a substitute item.

Using a user-scanned barcode of an item during shopping further includes tracking a total cost of one or more selected items. Also, one or more embodiments of the invention include using the barcode-based shopping cart tracker module during checkout to provide a shopping cart list to a checkout assistant module along with any coupons to be used to verify if the checkout is correct.

The techniques depicted in FIG. 6 and FIG. 7 can also, as described herein, include providing a system, wherein the system includes distinct software modules, each of the distinct software modules being embodied on a tangible computer-readable recordable storage medium. All the modules (or any subset thereof) can be on the same medium, or each can be on a different medium, for example. The modules can include any or all of the components shown in the figures. In one or more embodiments, the modules include a guideline manager module, a profile manager module, a shopping list manager module, an inter-store planner module, and an intra-store planner module that can run, for example on one or more hardware processors. The method steps can then be carried out using the distinct software modules of the system, as described above, executing on the one or more hardware processors. Further, a computer program product can include a tangible computer-readable recordable storage medium with code adapted to be executed to carry out one or more method steps described herein, including the provision of the system with the distinct software modules.

Additionally, the techniques depicted in FIG. 6 and FIG. 7 can be implemented via a computer program product that can include computer useable program code that is stored in a computer readable storage medium in a data processing system, and wherein the computer useable program code was downloaded over a network from a remote data processing system. Also, in one or more embodiments of the invention, the computer program product can include computer useable program code that is stored in a computer readable storage medium in a server data processing system, and wherein the computer useable program code are downloaded over a network to a remote data processing system for use in a computer readable storage medium with the remote system.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

One or more embodiments of the invention, or elements thereof, can be implemented in the form of an apparatus including a memory and at least one processor that is coupled to the memory and operative to perform exemplary method steps.

Figure 8:
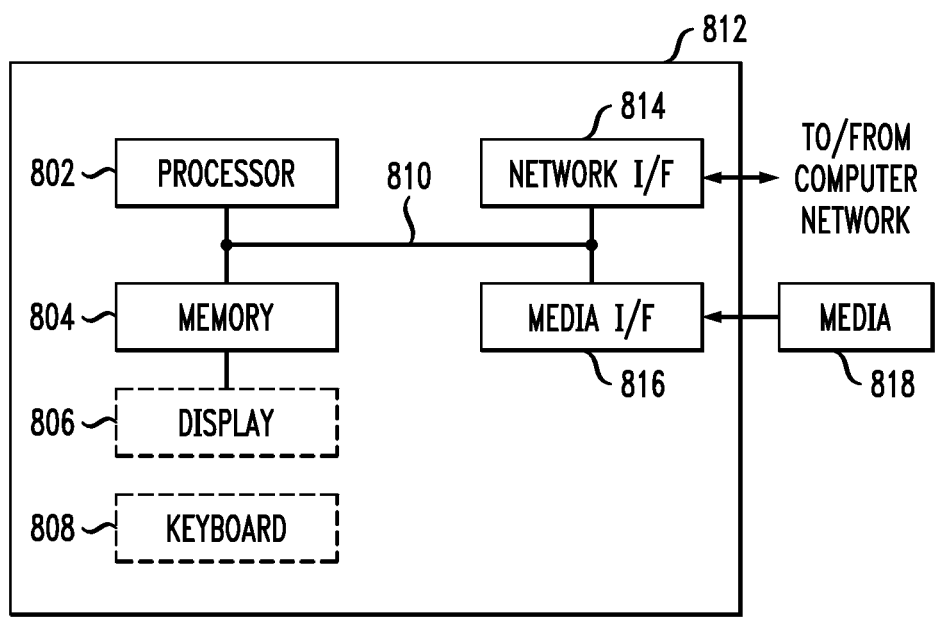
FIG. 8 is a system diagram of an exemplary computer system on which at least one embodiment of the invention can be implemented.

One or more embodiments can make use of software running on a general purpose computer or workstation. With reference to FIG. 8, such an implementation might employ, for example, a processor 802, a memory 804, and an input/output interface formed, for example, by a display 806 and a keyboard 808. The term "processor" as used herein is intended to include any processing device, such as, for example, one that includes a CPU (central processing unit) and/or other forms of processing circuitry. Further, the term "processor" may refer to more than one individual processor.

The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, one or more mechanisms for inputting data to the processing unit (for example, mouse), and one or more mechanisms for providing results associated with the processing unit (for example, printer). The processor 802, memory 804, and input/output interface such as display 806 and keyboard 808 can be interconnected, for example, via bus 810 as part of a data processing unit 812. Suitable interconnections, for example via bus 810, can also be provided to a network interface 814, such as a network card, which can be provided to interface with a computer network, and to a media interface 816, such as a diskette or CD-ROM drive, which can be provided to interface with media 818.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 802 coupled directly or indirectly to memory elements 804 through a system bus 810. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including but not limited to keyboards 808, displays 806, pointing devices, and the like) can be coupled to the system either directly (such as via bus 810) or through intervening I/O controllers (omitted for clarity).

Network adapters such as network interface 814 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 812 as shown in FIG. 8) running a server program. It will be understood that such a physical server may or may not include a display and keyboard.

As noted, aspects of the present invention may take the form of a computer program product embodied in one or more computer readable medium(s) having computer readable program code embodied thereon. Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Media block 818 is a non-limiting example. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, radio frequency (RF), etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, component, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be noted that any of the methods described herein can include an additional step of providing a system comprising distinct software modules embodied on a computer readable storage medium; the modules can include, for example, any or all of the components shown in the figures detailed herein and corresponding descriptions thereof. The method steps can then be carried out using the distinct software modules and/or sub-modules of the system, as described above, executing on one or more hardware processors 802. Further, a computer program product can include a computer-readable storage medium with code adapted to be implemented to carry out one or more method steps described herein, including the provision of the system with the distinct software modules.

In any case, it should be understood that the components illustrated herein may be implemented in various forms of hardware, software, or combinations thereof; for example, application specific integrated circuit(s) (ASICS), functional circuitry, one or more appropriately programmed general purpose digital computers with associated memory, and the like. Given the teachings of the invention provided herein, one of ordinary skill in the related art will be able to contemplate other implementations of the components of the invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

At least one embodiment of the invention may provide one or more beneficial effects, such as, for example, evidence-based shopping list creation and location-based food purchasing guidance.

It will be appreciated and should be understood that the exemplary embodiments of the invention described above can be implemented in a number of different fashions. Given the teachings of the invention provided herein, one of ordinary skill in the related art will be able to contemplate other implementations of the invention. Indeed, although illustrative embodiments of the present invention have been described herein with reference to the accompanying drawings, it is to be understood that the invention is not limited to those precise embodiments, and that various other changes and modifications may be made by one skilled in the art.

What is claimed is:

1. A computer program product comprising a non-transitory computer readable recordable storage medium including computer useable program code for generating location-based food purchase guidance, the computer program product including:

computer useable program code for obtaining (i) a shopping list comprising multiple food items and one or more available replacement food items associated with each of the multiple food items based on nutritional composition, and (ii) a list of multiple stores to be considered in connection with the shopping list;

computer useable program code for generating a user interface to enable user input and user manipulation of a guideline-based shopping list, wherein said user interface comprises at least (i) a first component displaying the multiple food items on the guideline-based shopping list to the user in an order based on a user-generated preference list of food items, (ii) a second component that is linked to a nutritional database comprising nutritional information pertaining to each item on the guideline-based shopping list, and (iii) a third component that is linked to a customer review database comprising one or more customer reviews pertaining to each item on the guideline-based shopping list;

computer useable program code for automatically filtering out one or more of the multiple food items that are not suitable for the user, based on user input via the user interface, to produce an updated guideline-based shopping list for the user;

computer useable program code for using the updated shopping list, the list of multiple stores, a store location map and inter-store routing guidance to generate an inter-store shopping route; and computer useable program code for generating an in-store shopping route, for each of the multiple stores in the inter-store shopping route, based on (i) the updated shopping list, (ii) intra-store routing guidance for each of the multiple stores based on a preferred purchasing order of the multiple food items on the updated guideline-based shopping list based on a temperature category of each of the multiple food items, and (iii) a floor plan for the store.

2. The computer program product of claim 1, wherein generating the in-store shopping route further comprises using one or more user preferences in connection with the intra-store guidance.

3. A system for guideline-based nutrition management, comprising:
a memory; and
at least one processor coupled to the memory and configured to:
use user-provided information and nutrition information to generate a set of one or more personalized nutrition guidelines for a user;
use the user-provided information and the set of one or more personalized nutrition guidelines for the user to generate a user profile, wherein the user profile comprises (i) one or more shopping preferences, (ii) health information including present user health status and family medical history of the user, and (iii) one or more nutrition preferences;
use the personalized set of one or more nutrition guidelines and the user profile to generate a guideline-based shopping list for the user, wherein said guideline-based shopping list comprises (i) multiple food items and (ii) one or more available replacement food items associated with each of the multiple food items based on nutritional composition;
generate a user interface to enable user input and user manipulation of the guideline-based shopping list, wherein said user interface comprises at least (i) a first component displaying the multiple food items on the guideline-based shopping list to the user in an order based on a user-generated preference list of food items, (ii) a second component that is linked to a nutritional database comprising nutritional information pertaining to each item on the guideline-based shopping list, and (iii) a third component that is linked to a customer review database comprising one or more customer reviews pertaining to each item on the guideline-based shopping list;
automatically filter out one or more of the multiple food items that are not suitable for the user, based on user input via the user interface, to produce an updated guideline-based shopping list for the user;
use the updated guideline-based shopping list, a list of one or more stores, a store location map and inter-store routing guidance to generate an inter-store shopping route;
generate an in-store shopping route, for each of the one or more stores in the inter-store shopping route, based on (i) the updated shopping list, (ii) intra-store routing guidance based on a preferred purchasing order of the multiple food items on the updated guideline-based shopping list based on a temperature category of each of the multiple food items, and (iii) a floor plan for the store; and
perform nutrition compliance tracking for the user based on one or more tracked food items and one or more tracked exercise activities.

4. The system of claim 3, wherein generating the personalized set of one or more nutrition guidelines and generating the user profile comprise using Web-enabled questionnaires to collect and assess information pertaining to the user.

5. The system of claim 3, wherein using the personalized set of one or more nutrition guidelines and the user profile to generate the guideline-based shopping list comprises using information pertaining to availability of one or more selected food markets based on the personalized set of one or more nutrition guidelines.

6. The system of claim 3, wherein using the personalized set of one or more nutrition guidelines and the user profile to generate the guideline-based shopping list comprises accessing a food market supply list repository and dividing candidate food into one or more categories.

7. The system of claim 3, wherein generating the guideline-based shopping list further comprises using additional user input pertaining to user budget, travel distance of one or more stores, user preference of one or more stores, and available coupons from one or more stores.

8. The system of claim 3, wherein generating the guideline-based shopping list further comprises facilitating a user to interactively select one or more items to purchase, and updating a food compliance report in real-time and providing one or more food suggestions to the user based on the one or more selected items.

* * * * *